US00PP26009P2

(12) United States Plant Patent
Li

(10) Patent No.: US PP26,009 P2
(45) Date of Patent: Oct. 20, 2015

(54) ***VERBENA* PLANT NAMED 'KLEVP14463'**

(50) Latin Name: ***Verbena* sp.**
Varietal Denomination: KLEVP14463

(71) Applicant: Klemm+Sohn GmbH & Co. KG, Stuttgart (DE)

(72) Inventor: Ruijun Li, North Parramata (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 28 days.

(21) Appl. No.: 14/120,220

(22) Filed: May 7, 2014

(51) Int. Cl.
*A01H 5/02* (2006.01)

(52) U.S. Cl.
USPC ..... Plt./308

(58) Field of Classification Search
USPC ..... Plt./308
CPC ..... A01H 5/02; A01H 5/00
See application file for complete search history.

*Primary Examiner* — Kent L Bell
(74) *Attorney, Agent, or Firm* — James M. Weatherly; Barbara Campbell; Cochran Freund & Young, LLC

(57) ABSTRACT

A new *Verbena* plant particularly distinguished by large pink and white flowers having good color contrast, good branching and an early flowering time, is disclosed.

1 Drawing Sheet

Genus and species: *Verbena* sp.
Variety denomination: 'KLEVP14463'.

BACKGROUND OF THE NEW PLANT

The present invention comprises a new and distinct variety of *Verbena*, botanically known as *Verbena* sp., and hereinafter referred to by the variety name 'KLEVP14463'. 'KLEVP 14463' originated from a cross-pollination conducted in April 2010 in Sydney, Australia between the proprietary female *Verbena* variety '001.1.42' (unpatented), and the proprietary male *Verbena* variety derived from the cross of 'V9120' (unpatented).

The seeds from the cross were sown and plants were grown for evaluation, where an individual plant designated 'KLEVP14463' was selected from the group of plants in Cobitty, NSW, Australia in September 2011.

In September 2011, 'KLEVP14463' was first vegetatively propagated by vegetative cuttings in Cobitty, NSW, Australia. 'KLEVP14463' was found to reproduce true to type in successive generations of asexual propagation via vegetative cuttings in Stuttgart, Germany.

CROSS REFERENCE TO RELATED APPLICATIONS

Plant Breeder's Rights for 'KLEVP14463' were applied for in Canada on Feb. 24, 2014, application number 14-8210. 'KLEVP14463' has not been made publicly available or sold more than one year prior to the filing date of this application.

SUMMARY

The following are the most outstanding and distinguishing characteristics of this new variety when grown under normal horticultural practices in Stuttgart, Germany.

1. Large pink and white flowers having good color contrast;
2. Good branching; and
3. An early flowering time.

DESCRIPTION OF THE PHOTOGRAPH

This new *Verbena* plant is illustrated by the accompanying photograph which shows the plant's overall plant habit including form, foliage, and flowers.

The photograph is of a four to five-month-old plant grown in a greenhouse in Stuttgart, Germany in August 2013. The colors shown are as true as can be reasonably obtained by conventional photographic procedures.

DESCRIPTION OF THE NEW VARIETY

The following detailed descriptions set forth the distinctive characteristics of 'KLEVP14463'. The data which define these characteristics were collected from asexual reproductions carried out in Stuttgart, Germany. Data was collected on three-month-old plants grown in a greenhouse in Stuttgart, Germany in February 2014. Color references are to The R.H.S. Colour Chart of The Royal Horticultural Society of London (R.H.S.) (2005).

Classification:
- *Family*.—Verbenaceae.
- *Botanical*.—*Verbena* sp.
- *Common*.—*Verbena*.
- *Designation*.—'KLEVP14463'.

Parentage:
- *Female parent*.—The proprietary *verbena* variety '001.1.42' (unpatented).
- *Male parent*.—The proprietary male *verbena* variety 'V9120' (unpatented).

Plant:
- *Growth and branching habit*.—Trailing.
- *Height (from top of soil)*.—20.0 cm.
- *Width (horizontal plant diameter)*.—40.0 cm.
- *Time to produce a finished flowering plant*.—About 8 weeks.
- *Time to initiate and develop roots*.—3 weeks.
- *Root description*.—White.

Stems:
*Number of branches per plant*.—Less than 40.
*Growth habit*.—Trailing.
*Length*.—25.0 cm.
*Diameter*.—1.0 cm.
*Internode length*.—2.0 cm.
*Color*.—RHS 130D.
*Anthocyanin*.—Absent.
*Texture and appearance*.—Pubescence, round.
*Pubescence color*.—RHS 130 D.

Leaves:
*Arrangement*.—Opposite.
*Immature and mature leaf*.—Color: Upper surface: RHS 141A. Lower surface: RHS 141C.
*Length*.—2.5 cm.
*Width*.—1.5 cm.
*Shape*.—Lanceolate.
*Apex*.—Acute.
*Base*.—Obtuse.
*Margin*.—Serrate.
*Texture*.—Upper surface: Leathery. Lower surface: Rugose.
*Venation type*.—Pinnate.
*Venation color*.—Upper and lower surfaces: RHS 141D.
*Petioles*.—Length: 1.0 cm. Diameter: 0.1 cm. Color: RHS 141D. Texture: Leathery.

Flower buds:
*Shape*.—Tall, cylindrical.
*Length*.—0.5 cm.
*Diameter*.—0.1 cm.
*Color* (*at tight bud*).—RHS 75C.

Inflorescence:
*Blooming habit* (*flowering season*).—Continuously.
*Lastingness of individual blooms on the plant*.—2 weeks.
*Fragrance*.—Absent.
*Inflorescence type*.—Umbel.
*Length of inflorescence*.—6.0 cm.
*Diameter of inflorescence*.—6.0 cm.
*Number of florets per inflorescence*.—Greater than 15.
*Peduncle*.—Color: RHS 141A. Length: 4.0 cm. Diameter: 0.1 cm.

Florets:
*Length*.—2.0 cm.
*Diameter*.—4.0 cm.
*Texture*.—Glossy.
*Form*.—Umbel.
*Length*.—0.1 cm.
*Diameter*.—4.0 cm.
*Color*.—Immature: Upper surface: RHS 55A, RHS 75C and RHS 999D. Lower surface: RHS 55D, RHS 75D and RHS 999D. Mature: Upper and lower surfaces: RHS 55B, RHS 75D and RHS 999D.
*Corolla tube length*.—0.2 cm.
*Corolla tube color*.—RHS 55B.
*Petals*.—Length of lobe: 2.0 cm. Diameter of lobe: 2.0 cm. Lobe shape: Round. Apex: Acute. Base: Obtuse. Margin: Entire. Texture: Upper and lower surfaces: Glossy, satiny.
*Pedicels*.—Length: 2.0 cm. Diameter: About 1.0 cm. Color: RHS 55B. Texture and appearance: Hairy, dull. Arrangement: Round.

Sepals:
*Shape*.—Lanceolate.
*Apex*.—Acute.
*Base*.—Obtuse.
*Margin*.—Entire.
*Length*.—2.0 cm.
*Diameter*.—0.5 cm.
*Color*.—RHS 141C.
*Texture*.—Upper and lower surfaces: Hairy, dull.

Reproductive organs:
*Stamens*.—Present.
*Quantity*.—Numerous.
*Anther*.—Shape: Elliptic. Color: RHS 141D. Length: Less than 0.1 cm. Diameter: 0.1 cm.
*Pollen amount*.—Absent.
*Pistils*.—Number: 1. Length: 1.0 cm. Diameter: Less than 0.1 cm. Stigma: Color: RHS 141D. Appearance: Ovate. Length: Less than 0.1 cm. Diameter: Less than 0.1 cm. Style: Color: RHS 141D. Length: 0.2 cm. Diameter: Less than 0.1 cm. Appearance: Long.

Fruit and seed set: Absent.

Disease and pest/insect resistance: Resistant to mildew.

COMPARISON WITH PARENTAL LINES AND KNOWN VARIETIES

'KLEVP14463' is distinguished from its parents as described in Table 1.

TABLE 1

Comparison with Parental Lines

| Trait | Variety 'KLEVP14463' | Female parent '001.1.42' | Male Parent 'V9120' |
|---|---|---|---|
| Color contrast | Good contrast | Little contrast | Little contrast |
| earliness | Early | Medium | Very early |

'KLEVP14463' is most similar to the commercial *verbena* Lanai Pink Twister (patent status unknown). Differences between the varieties are described in Table 2.

TABLE 2

Comparison with Similar Variety

| Trait | Variety 'KLEVP14463' | Commercial line 'Lanai Pink Twister' |
|---|---|---|
| Branching | Good branching | Weaker branching than 'KLEVP14463' |
| Earliness (flowering time) | Earlier than 'Lanai Pink Twister' | Later than 'KLEVP14463' |
| Flower size | Bigger than 'Lanai Pink Twister' | Smaller than 'KLEVP14463' |

I claim:

1. A new and distinct variety of *Verbena* plant designated 'KLEVP14463' as shown and described herein.

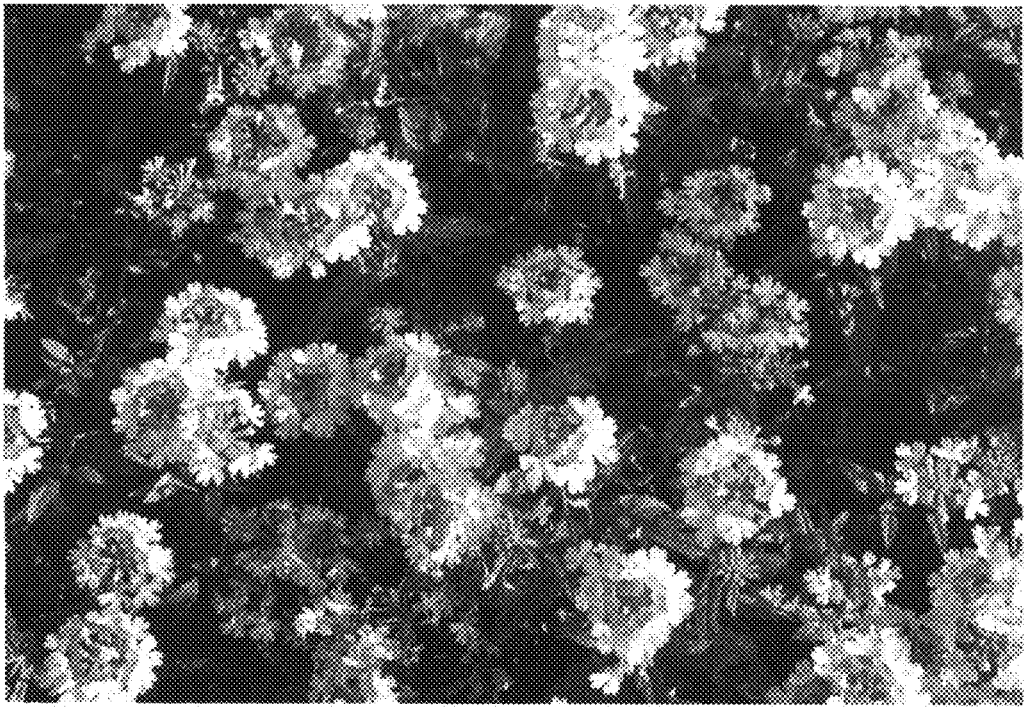

* * * * *